US011819653B2

(12) United States Patent
Ivosevic (10) Patent No.: US 11,819,653 B2
(45) Date of Patent: *Nov. 21, 2023

(54) ADAPTER CAP FOR DRUG TRANSFER ASSEMBLY

(71) Applicant: Becton Dickinson and Company Limited, Dun Laoghaire (IE)

(72) Inventor: Milan Ivosevic, Kinnelon, NJ (US)

(73) Assignee: Becton Dickinson and Company Limited, Dun Laoghaire (IE)

( * ) Notice: Subject to any disclaimer, the term of this patent is extended or adjusted under 35 U.S.C. 154(b) by 362 days.

This patent is subject to a terminal disclaimer.

(21) Appl. No.: 16/523,092

(22) Filed: Jul. 26, 2019

(65) Prior Publication Data

US 2019/0344066 A1 Nov. 14, 2019

Related U.S. Application Data

(63) Continuation of application No. 14/022,764, filed on Sep. 10, 2013, now Pat. No. 10,406,344.

(60) Provisional application No. 61/699,457, filed on Sep. 11, 2012.

(51) Int. Cl.
| | |
|---|---|
| *A61M 39/20* | (2006.01) |
| *A61M 5/14* | (2006.01) |
| *A61M 5/158* | (2006.01) |
| *A61M 39/02* | (2006.01) |

(52) U.S. Cl.
CPC .......... *A61M 39/20* (2013.01); *A61M 5/1413* (2013.01); *A61M 5/158* (2013.01); *A61M 2039/0205* (2013.01); *A61M 2205/0216* (2013.01)

(58) Field of Classification Search
CPC .......... A61M 39/20; A61M 2039/0205; A61M 5/158; A61M 5/1413; A61M 2205/0216
See application file for complete search history.

(56) References Cited

U.S. PATENT DOCUMENTS

| | | | |
|---|---|---|---|
| 2,573,552 | A | 10/1951 | Detzel |
| 3,219,036 | A | 11/1965 | Stafford |
| 3,307,552 | A | 3/1967 | Strawn |

(Continued)

FOREIGN PATENT DOCUMENTS

| | | |
|---|---|---|
| EP | 0309426 A2 | 3/1989 |
| EP | 0327079 A2 | 8/1989 |

(Continued)

*Primary Examiner* — Tiffany Legette
(74) *Attorney, Agent, or Firm* — The Webb Law Firm (57) ABSTRACT

A drug transfer assembly including a connector connectable to a portion of an intravenous line adapted for connection to a patient's bloodstream and an adapter cap removably connectable with the connector is disclosed. The connector is formed of a rigid material and the adapter cap is formed of a pliable material. With the adapter cap connected to the connector, the adapter cap protectively surrounds and shields the connector. The adapter cap provides a cushioning surface which prevents rubbing of the connector against the skin of a patient. In this manner, the adapter cap prevents the connector of a drug transfer assembly from causing irritation and/or infection to the skin of a patient. Furthermore, the adapter cap provides a protective shield which prevents the connector of a drug transfer assembly from becoming contaminated with undesirables.

18 Claims, 11 Drawing Sheets

(56) References Cited

U.S. PATENT DOCUMENTS

| | | | |
|---|---|---|---|
| 4,132,225 A | 1/1979 | Whattam | |
| 4,440,207 A | 4/1984 | Genatempo et al. | |
| 4,850,393 A | 7/1989 | Lashomb | |
| 5,004,113 A | 4/1991 | Nogawa | |
| 5,280,809 A | 1/1994 | Tive | |
| 5,382,242 A | 1/1995 | Horton et al. | |
| 5,413,561 A | 5/1995 | Fischell et al. | |
| 5,735,826 A | 4/1998 | Richmond | |
| 5,908,048 A | 6/1999 | Van Driel | |
| 6,551,286 B1 | 4/2003 | Claessens | |
| 6,645,195 B1 | 11/2003 | Bhat et al. | |
| 2001/0039402 A1* | 11/2001 | Prais | B24B 19/16 604/239 |
| 2001/0051789 A1 | 12/2001 | Parsons | |
| 2003/0109853 A1 | 6/2003 | Harding et al. | |
| 2003/0191445 A1 | 10/2003 | Wallen et al. | |
| 2006/0065677 A1 | 3/2006 | Py et al. | |
| 2006/0089606 A1* | 4/2006 | Tsai | A61M 5/1408 604/256 |
| 2007/0112333 A1 | 5/2007 | Hoang et al. | |
| 2008/0027410 A1 | 1/2008 | Harding et al. | |
| 2008/0116647 A1 | 5/2008 | Anderson et al. | |
| 2008/0172007 A1 | 7/2008 | Bousquet | |
| 2009/0105665 A1 | 4/2009 | Wang et al. | |
| 2009/0137969 A1 | 5/2009 | Colantonio et al. | |
| 2009/0171297 A1 | 7/2009 | Smith et al. | |
| 2010/0286663 A1 | 11/2010 | Mishima et al. | |
| 2011/0106060 A1 | 5/2011 | Atkinson et al. | |
| 2011/0240162 A1* | 10/2011 | Zeyfang | A61M 39/20 138/89.2 |
| 2011/0270196 A1 | 11/2011 | Valaie | |
| 2012/0130329 A1* | 5/2012 | March | F16K 3/24 604/332 |

FOREIGN PATENT DOCUMENTS

| | | |
|---|---|---|
| JP | 59118159 A | 7/1984 |
| JP | 201022511 A | 2/2010 |

\* cited by examiner

ADAPTER CAP FOR DRUG TRANSFER ASSEMBLY

CROSS-REFERENCE TO RELATED APPLICATIONS

This application in a continuation of U.S. patent application Ser. No. 14/022,764, filed Sep. 10, 2013, which claims priority to U.S. Provisional Patent Application Ser. No. 61/699,457, filed Sep. 11, 2012, the entire disclosures of each of which are hereby expressly incorporated by reference herein.

BACKGROUND OF THE INVENTION

1. Field of the Disclosure

The present disclosure relates generally to a drug transfer assembly. More particularly, the present disclosure relates to an adapter cap for protectively surrounding and shielding a connector which provides a leakproof seal throughout a drug transfer procedure.

2. Description of the Related Art

Personal intravenous therapy applications allow patients to receive infusion and medication treatment at home. For example, home therapy may include the administration of medications by IV using intravenous and subcutaneous or hypodermis routes, i.e., into the bloodstream and under the skin. Examples of medical treatments that personal intravenous therapy applications may provide to a patient include antibiotics, pain management medications, cancer treatments, and similar medications. Personal intravenous therapy applications allow for more cost-effective medical treatments and reduce the duration of an in-patient hospital stay. Additionally, returning to a patient's home and family can promote quicker recovery and improve a patient's quality of life.

In such applications, drug-delivery devices store drugs until the drugs are required by a user. For example, a syringe assembly may contain medications required by a user. A patient is provided with a personal intravenous system that may include intravenous tubing and a connector that is adapted to receive an injector and/or syringe assembly containing a required medication. In this manner, when a treatment is needed, a user is able to connect a syringe assembly to the connector and then inject a medication intravenously to the user via the injector and/or syringe assembly, the connector, and the intravenous tubing. However, the connector of a personal intravenous system that is carried by a patient may cause irritation to a patient's skin due to its rigid material and/or its sharp edges. Furthermore, the connector may get contaminated with undesirables.

SUMMARY OF THE INVENTION

The present disclosure provides a drug transfer assembly including a connector connected to a portion of an intravenous line adapted for connection to a patient's bloodstream and an adapter cap removably connectable with the connector. The connector is formed of a rigid material and the adapter cap is formed of a pliable material. With the adapter cap connected to the connector, the adapter cap protectively surrounds and shields the connector. The adapter cap provides a cushioning surface which prevents rubbing of the connector against the skin of a patient. In this manner, the adapter cap prevents the connector of a drug transfer assembly from causing irritation and/or infection to the skin of a patient. Furthermore, the adapter cap provides a protective shield which prevents the connector of a drug transfer assembly from becoming contaminated with undesirables.

In accordance with an embodiment of the present invention, a drug transfer assembly includes an intravenous line adapted for connection to a bloodstream of a patient and a connector connected to a portion of the intravenous line, the connector having a connector material hardness. The drug transfer assembly includes an injector removably connectable with the connector, the injector containing a medication, and an adapter cap removably connectable with the connector, the adapter cap having an adapter cap material hardness, the adapter cap material hardness less than the connector material hardness. With the injector connected to the connector, the connector provides a closed connection to the injector and the intravenous line and the injector is in fluid communication with the intravenous line via the connector thereby allowing injection of the medication to the bloodstream of the patient, and with the adapter cap connected to the connector, the adapter cap protectively surrounds the connector.

In one configuration, the connector includes a rigid material and the adapter cap includes a pliable material. In one configuration, the intravenous line includes a flexible tubing. In another configuration, the injector includes a syringe assembly. In one configuration, the drug transfer assembly further includes a second connector connected to a second portion of the intravenous line, the second connector adapted to receive an intravenous bag containing a second medication. In another configuration, the adapter cap includes a thermoplastic elastomer. In yet another configuration, the adapter cap includes a thermosetting elastomer. In one configuration, the adapter cap has a hardness range between Shore A 5 and Shore A 50. In another configuration, the adapter cap has a hardness range between Shore A 20 and Shore A 40.

In accordance with another embodiment of the present invention, a drug transfer assembly includes an intravenous line adapted for connection to a bloodstream of a patient and a connector connected to a portion of the intravenous line, the connector having a connector material hardness. The drug transfer assembly includes an adapter cap removably connectable with the connector, the adapter cap having an adapter cap material hardness, the adapter cap material hardness less than the connector material hardness.

In one configuration, the drug transfer assembly further includes an injector removably connectable with the connector, the injector containing a medication. In another configuration, with the injector connected to the connector, the connector provides a closed connection to the injector and the intravenous line and the injector is in fluid communication with the intravenous line via the connector thereby allowing injection of the medication to the bloodstream of the patient, and with the adapter cap connected to the connector, the adapter cap protectively surrounds at least a portion of the connector. In yet another configuration, the injector includes a syringe assembly. In one configuration, the connector includes a rigid material and the adapter cap includes a pliable material. In another configuration, the intravenous line includes a flexible tubing.

In accordance with another embodiment of the present invention, an adapter cap for a drug transfer assembly includes a connector having a connector material hardness, the adapter cap being removably connectable with the connector, the adapter cap has an adapter cap material hardness, and the adapter cap material hardness is less than the connector material hardness.

In one configuration, with the adapter cap connected to the connector, the adapter cap protectively surrounds at least a portion of the connector. In another configuration, the connector includes a rigid material and the adapter cap includes a pliable material. In yet another configuration, the adapter cap has a hardness range between Shore A 5 and Shore A 50. In one configuration, the adapter cap has a hardness range between Shore A 20 and Shore A 40.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Referring to FIGS. 1-5, a drug transfer assembly 10 includes an intravenous line 12 adapted for connection to a bloodstream of a patient P. Drug transfer assembly 10 further includes a patient portion 13 of intravenous line 12, a first connector 14 connected to a first portion 16 of intravenous line 12, a second connector 18 connected to a second portion 20 of intravenous line 12, an intravenous line connector 22 for connecting in fluid communication patient portion 13 of intravenous line 12 with first portion 16 and second portion 20 of intravenous line 12, a patient connector 24 disposed at a patient end 26 of intravenous line 12, and an adapter cap 30 removably connectable with first connector 14.

Figure 1:
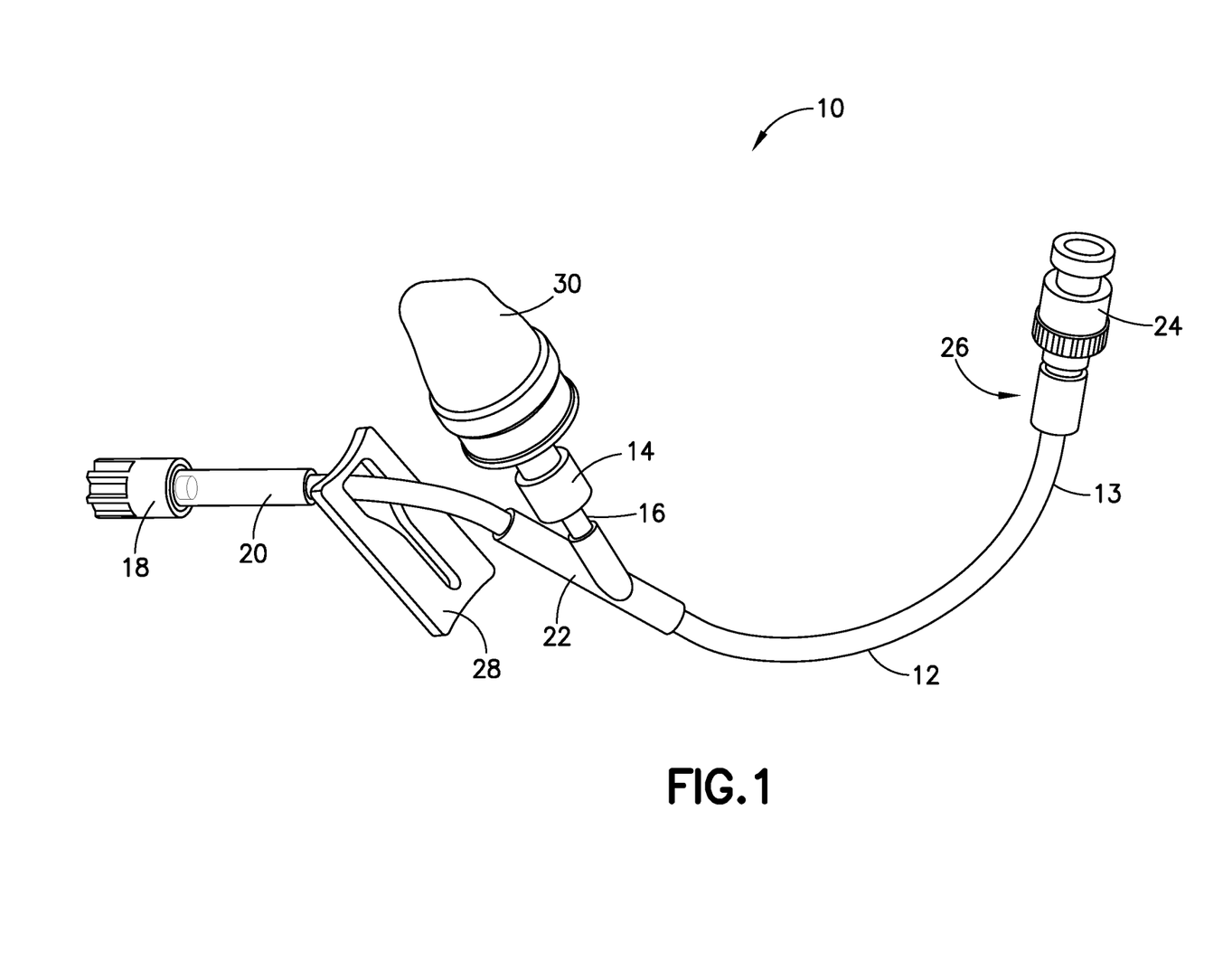
FIG. 1 is an assembled, perspective view of a drug transfer assembly in accordance with an embodiment of the present invention.
Figure 2A:
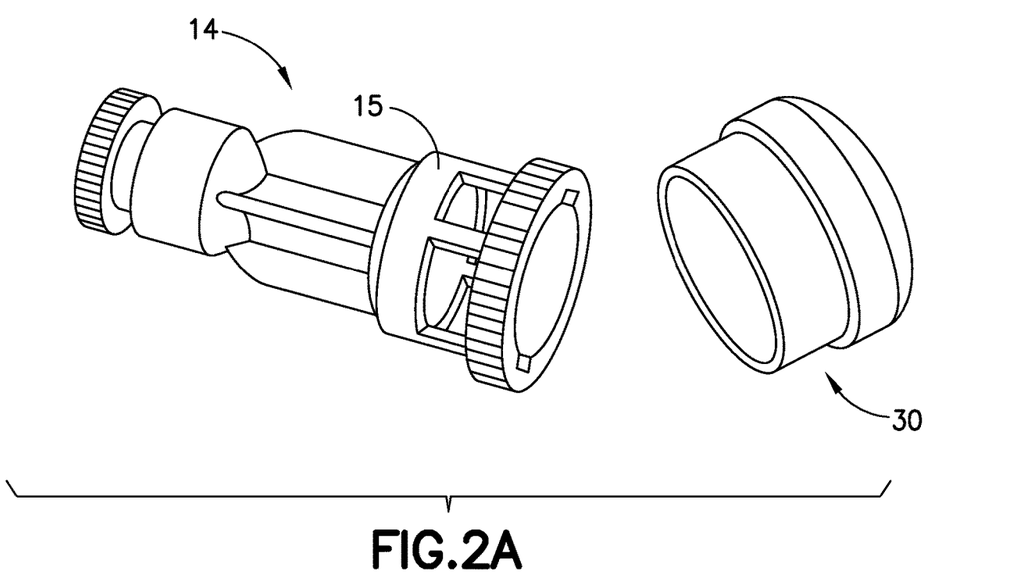
FIG. 2A is an exploded, perspective view of a connector and an adapter cap of a drug transfer assembly in accordance with an embodiment of the present invention
Figure 2B:
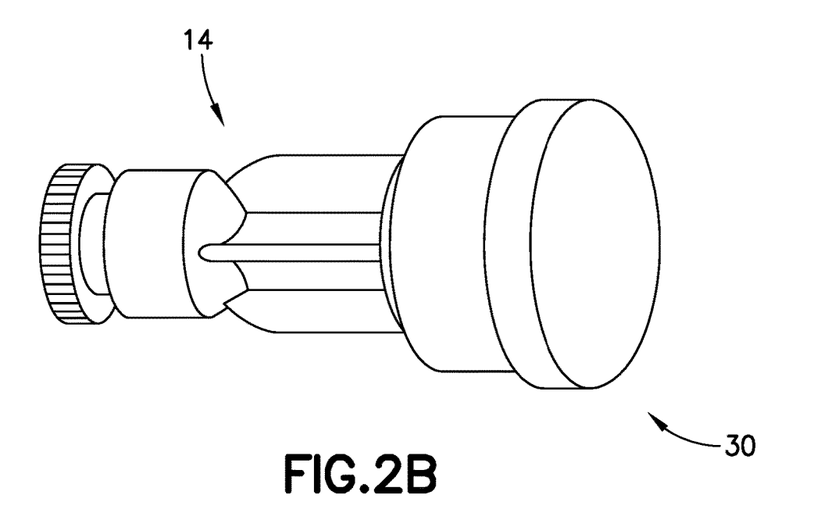
FIG. 2B is an assembled, perspective view of FIG. 2A with the adapter cap connected to the connector in accordance with an embodiment of the present invention.
Figure 3:
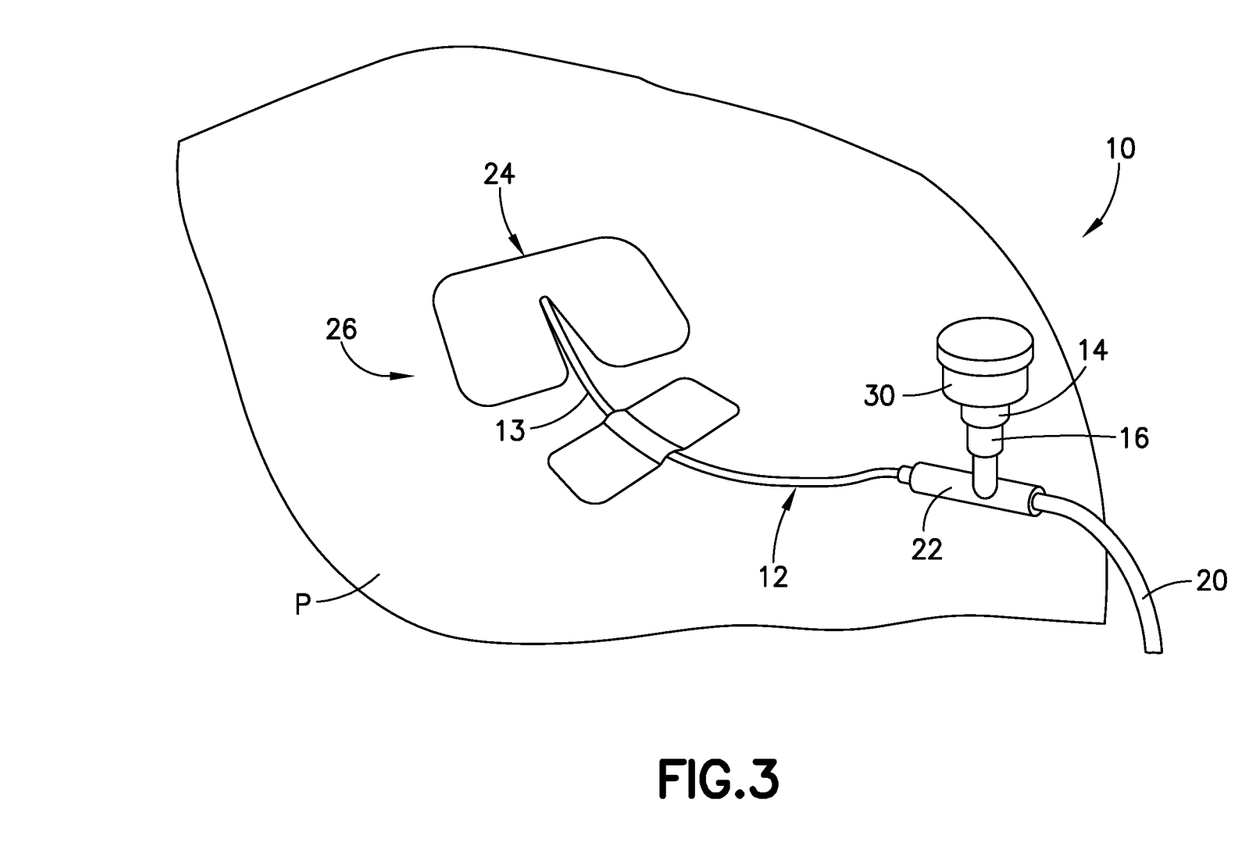
FIG. 3 is a perspective view of the drug transfer assembly of FIG. 1 with the drug transfer assembly provided to a patient in accordance with an embodiment of the present invention.
Figure 4:
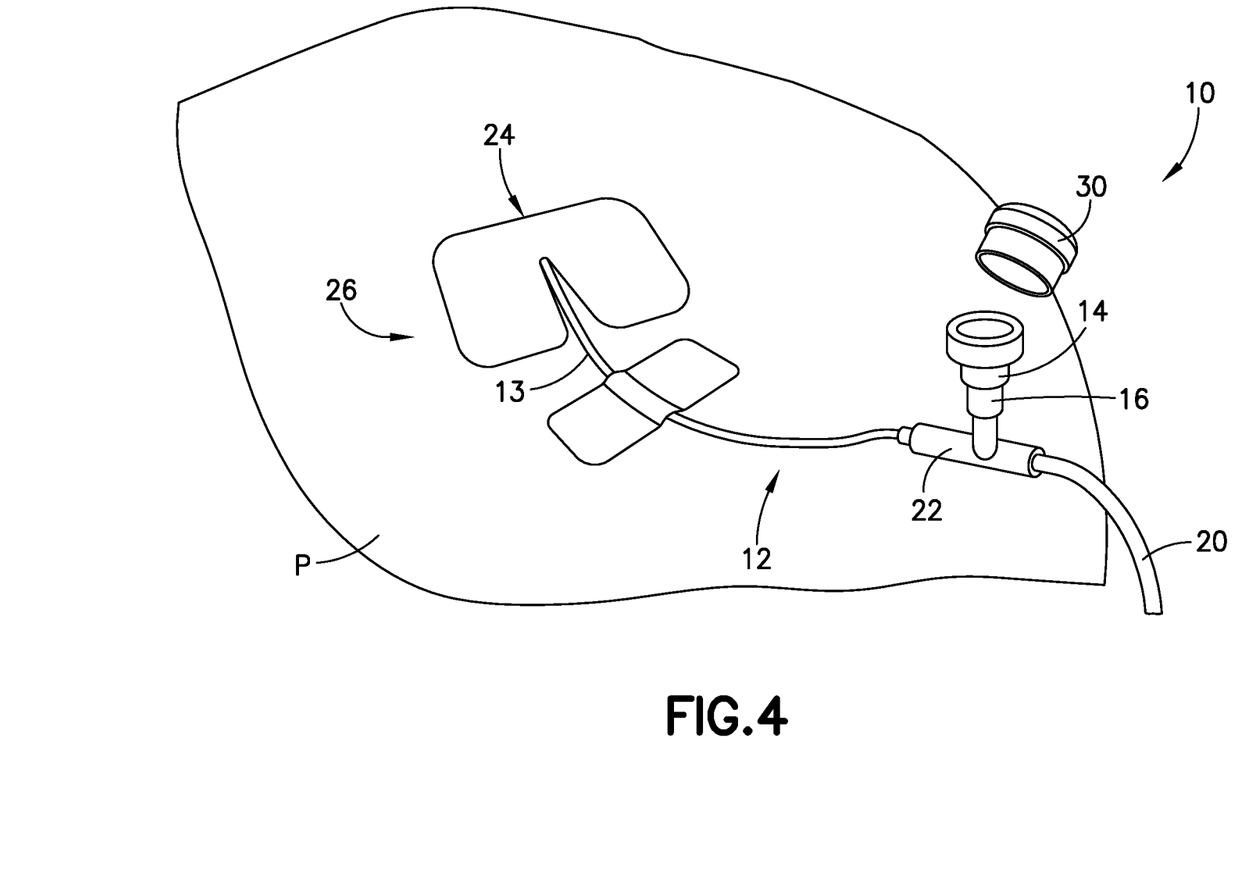
FIG. 4 is an exploded, perspective view of the drug transfer assembly of FIG. 3 with an adapter cap for connection with a connector of the drug transfer assembly removed in accordance with an embodiment of the present invention.
Figure 5:
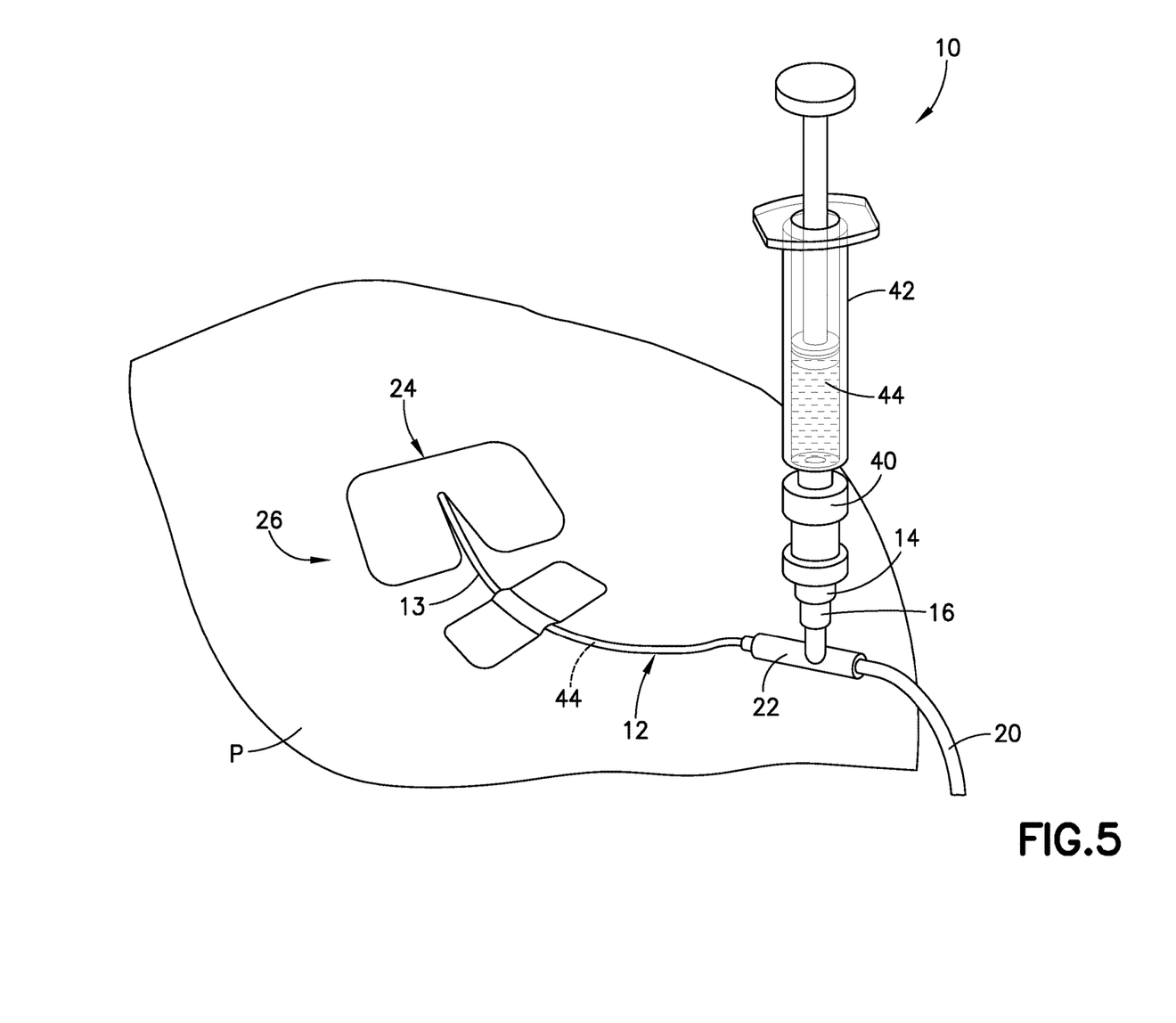
FIG. 5 is a perspective view of the drug transfer assembly of FIG. 3 with an injector connected to the connector of the drug transfer assembly in accordance with an embodiment of the present invention.

Referring to FIGS. 1-5, in one embodiment, intravenous line 12 may comprise sections of flexible plastic tubing. The sections of plastic tubing may be connected in fluid communication by intravenous line connector 22. In one embodiment, intravenous line connector 22 may comprise a Y-shape as shown in FIG. 1. In another embodiment, intravenous line connector 22 may comprise a T-shape as shown in FIGS. 3-5. Further, it is contemplated that intravenous line connector 22 may be made available in a variety of shapes and sizes to accommodate sections of plastic tubing so that first connector 14 and second connector 18 are spaced a distance from one another.

In one embodiment, first connector 14 comprises a PhaSeal connector which is compatible with a Becton Dickinson ("BD") PhaSeal™ System available from Becton, Dickinson and Company of Franklin Lakes, N.J., the assignee of the present invention. In other embodiments, first connector 14 comprises a connector which is compatible with other closed system drug transfer devices.

In one embodiment, second connector 18 comprises an intravenous bag connector which is adapted to receive an intravenous bag containing a second medication. In one embodiment, second connector 18 comprises a PhaSeal connector which is compatible with a Becton Dickinson ("BD") PhaSeal™ System available from Becton, Dickinson and Company of Franklin Lakes, N.J. In other embodiments, second connector 18 comprises a connector which is compatible with other closed system drug transfer devices.

Referring to FIG. 1, in one embodiment, drug transfer assembly 10 further includes a clamp 28 which can be used to temporarily restrict the flow of fluid within second portion 20 of the intravenous line 12.

The drug transfer assembly 10 of the present disclosure may be used with personal intravenous therapy applications that allow patients to receive infusion and medication treatment at home, although the drug transfer assembly 10 may also be used in other settings. Home therapies may include the administration of medications by IV using intravenous and subcutaneous or hypodermis routes, i.e., into the bloodstream and under the skin. Examples of medical treatments that personal intravenous therapy applications may provide to a patient include antibiotics, pain management medications, cancer treatments, and similar medications.

Medications may be packaged as "pre-filled" devices, wherein a syringe assembly is pre-filled with medication prior to being packaged and delivered to a patient. "Pre-filled" devices eliminate the need for a user to fill the device prior to injection.

Certain drugs or medications are preferably provided in powder or dry form (such as a lyophilized form), and require reconstitution prior to administration. Lyophilized drugs, for example, typically are supplied in a freeze-dried form that needs to be mixed with a diluent to reconstitute the substance into a form that is suitable for injection. In addition, drugs may be provided as multipart systems that require mixing prior to administration. For example, one or more liquid components, such as flowable slurries, and one or more dry components, such as powdered or granular components, may be provided in separate containers that require mixing prior to administration.

Referring to FIG. 5, drug transfer assembly 10 includes an injector 40 that is removably connectable with first connector 14 and a syringe assembly 42 containing a medication or fluid 44. Medication 44 can be packaged within syringe assembly 42 as a "pre-filled" device or medication 44 may be a reconstituted medication as discussed above. Once the medication 44 is contained within syringe assembly 42, the medication 44 is ready for administration to a bloodstream of a patient such as patient P (FIGS. 3-5). Once a patient is ready to administer the medication 44, the patient may remove an adapter cap 30 (FIG. 4) from first connecter 14 as will be described in further detail below.

Referring to FIG. 5, the patient P may then connect injector 40 to the first connector 14 that is connected to first portion 16 of intravenous line 12 of drug transfer assembly 10. Syringe assembly 42 may then be connected with injector 40. In one embodiment, injector 40 and syringe assembly 42 form a single component that is connected to first connector 14. With injector 40 connected to first connector 14, first connector 14 provides a secure, closed connection with injector 40 and syringe assembly 42 that provides a leakproof seal throughout a drug transfer procedure. Further, first connector 14 connects, in fluid communication, injector 40 and syringe assembly 42 with intravenous line 12 as shown in FIG. 5. In this manner, the patient P may inject medication 44 to their bloodstream. In such an embodiment, medication 44 can be injected into patient P through syringe assembly 42 to injector 40 to first connector 14 and through first portion 16 of intravenous line 12 to intravenous line connector 22 to patient portion 13 of intravenous line 12 and through patient connector 24 at patient end 26 of intravenous line 12 to the bloodstream of the patient P in a secured, leakproof, closed connection, i.e., in a manner such that no outside contaminants can enter into the drug transfer assembly 10 and such that no medication may leak from drug transfer assembly 10 during its travel through the above-described flow path.

Once the dose of medication has been administered, injector 40 and syringe assembly 42 are removed from first connector 14. In this configuration, first connector 14 is connected to first portion 16 of intravenous line 12 as shown in FIG. 3. A patient using a drug transfer assembly may have to carry drug transfer assembly 10 with first connector 14 on the patient's body. This may cause first connector 14, which is formed of a rigid material having a first connector material hardness, to contact an area of a patient's skin and cause irritation and/or infection to the patient. In one exemplary embodiment, first connector 14 is made from a material having a first connector material hardness that is greater than the adapter cap material hardness. For example, first connector 14 may be made from thermosetting polymers or thermoplastic polymers such as polypropylene, polyethylene, polystyrene, polycarbonate, acrylics, nylons, or similar materials. Furthermore, first connector 14 includes sharp edges which may contact an area of a patient's skin which may also cause irritation and/or infection to the patient. Additionally, when first connector 14 is exposed to the environment first connector 14 may become contaminated with undesirables.

To eliminate the above deficiencies of a drug transfer assembly, the adapter cap 30 of the present disclosure is connected to the first connector 14 when a patient is done administering a dose of medication as shown in FIG. 3. In this manner, adapter cap 30 protectively surrounds and shields the first connector 14 to prevent contact between first connector 14 and the skin of a patient and to prevent contamination of the first connector 14 of the drug transfer assembly 10.

Figure 6A:
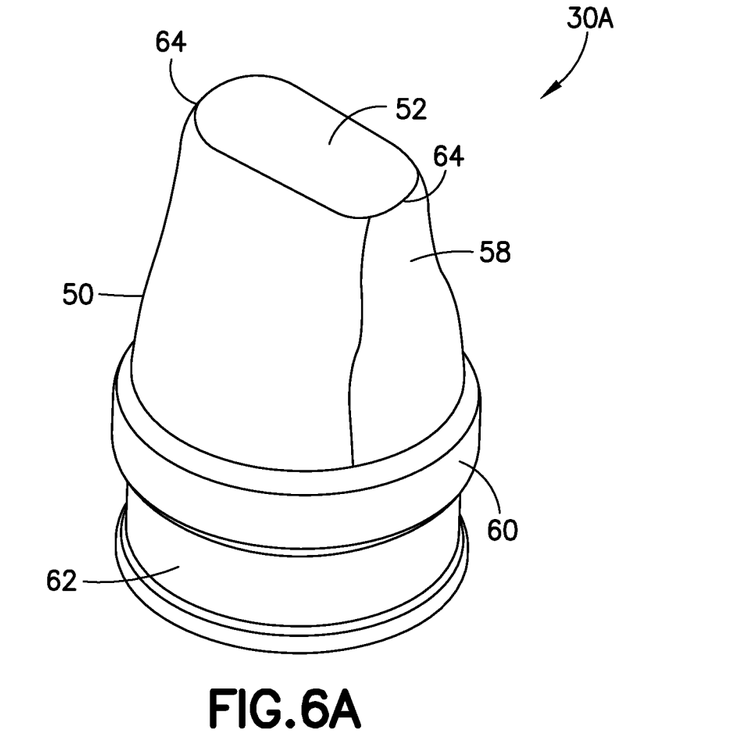
FIG. 6A is a perspective view of an adapter cap of a drug transfer assembly in accordance with an embodiment of the present invention.
Figure 6B:
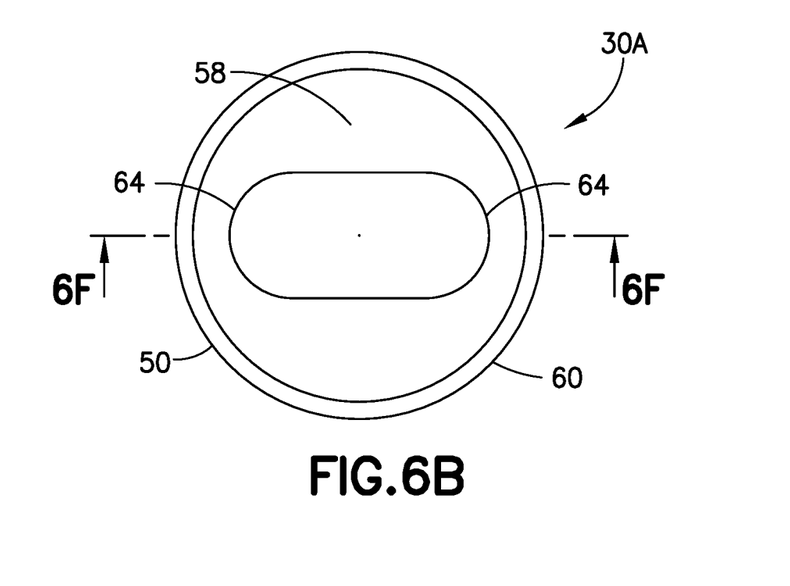
FIG. 6B is a plan view of the adapter cap of FIG. 6A in accordance with an embodiment of the present invention.
Figure 6C:
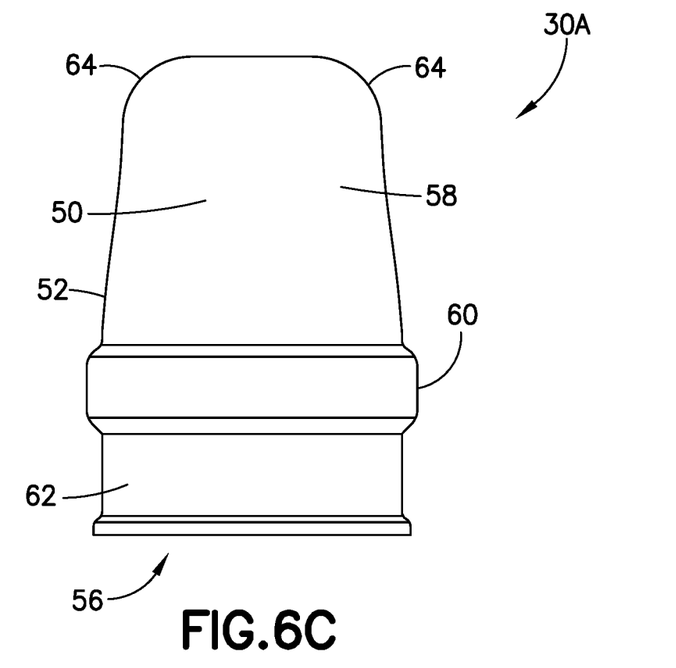
FIG. 6C is a front elevation view of the adapter cap of FIG. 6A in accordance with an embodiment of the present invention.
Figure 6D:
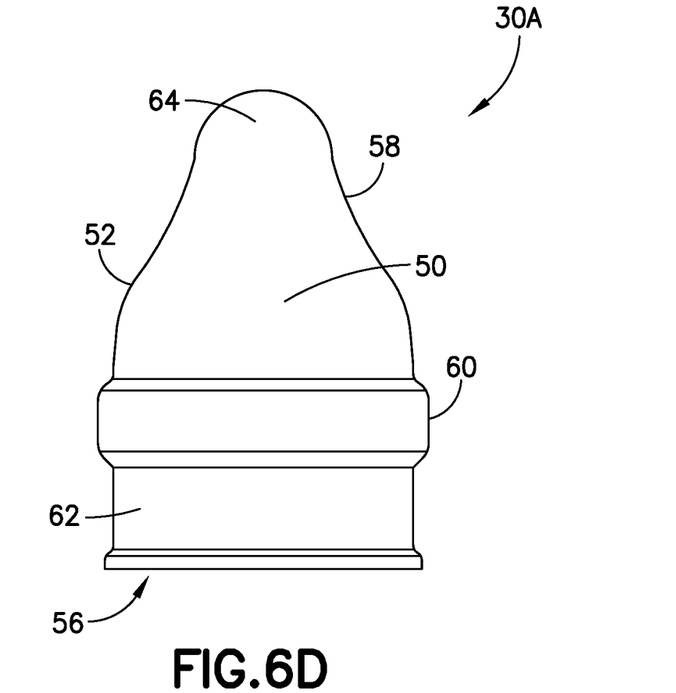
FIG. 6D is a side elevation view of the adapter cap of FIG. 6A in accordance with an embodiment of the present invention.
Figure 6E:
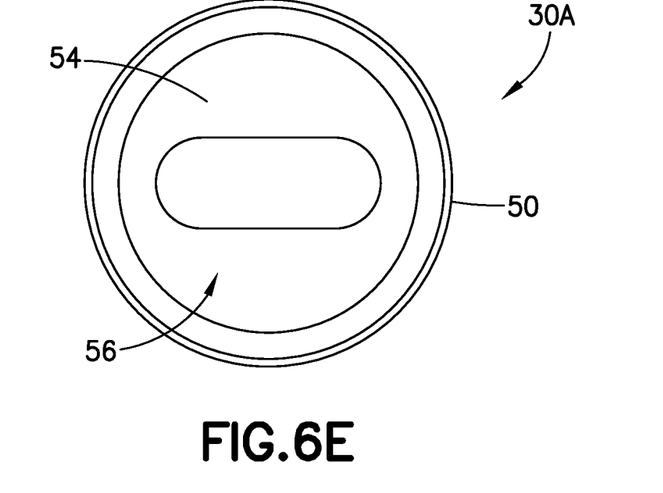
FIG. 6E is a bottom view of the adapter cap of FIG. 6A in accordance with an embodiment of the present invention.
Figure 6F:
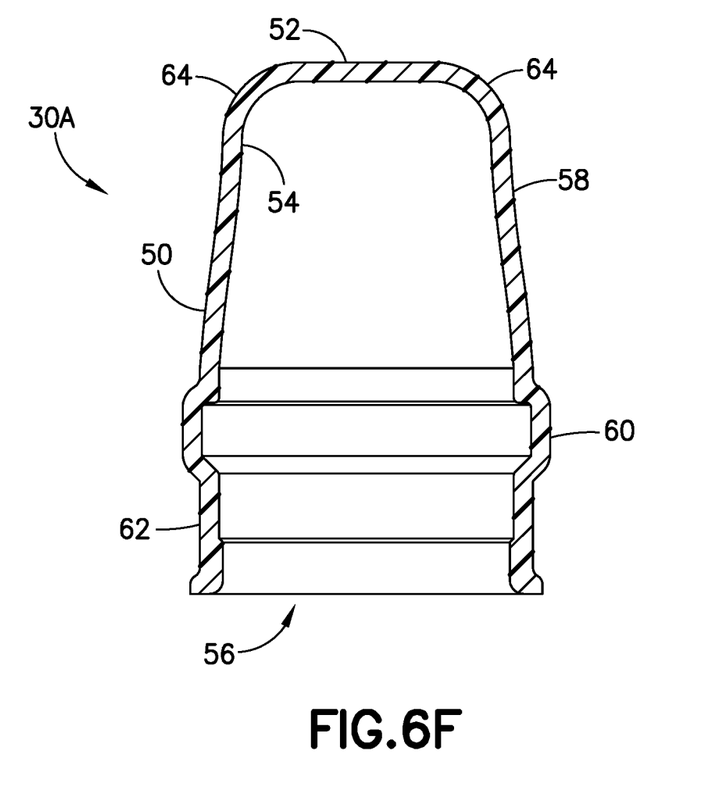
FIG. 6F is a cross-sectional view taken along line 6F-6F of the adapter cap of FIG. 6B in accordance with an embodiment of the present invention.

FIGS. 6A-6F illustrate an adapter cap 30A according to an exemplary embodiment of the present disclosure. Adapter cap 30A generally includes an adapter body 50 defining an adapter exterior wall 52 and an adapter interior wall 54, respectively corresponding to the exterior profile and the interior profile of adapter cap 30A. Referring to FIG. 6F, interior wall 54 defines a cavity 56 which is sized and shaped to receive first connector 14 via an interference fit connection as described below. Adapter body 50 generally includes a frustoconical tapered portion 58, a first cylindrical portion 60, a second cylindrical portion 62, and arcuate or curved edges 64. In this manner, adapter cap 30A does not have any sharp edges.

Adapter body 50 of an exemplary embodiment is preferably made of a pliable material, such as a soft rubber or pliable plastic, for example. In one exemplary embodiment, adapter body 50 is made from thermoplastic elastomers such as styrenic block copolymers, polyolefin blends & alloys, thermoplastic polyurethanes, thermoplastic copolyesters, thermoplastic polyamides, or similar materials. In other embodiments, adapter body 50 is made from thermosetting elastomers (rubbers) such as silicone, polyisoprene, neoprene, or similar materials. Adapter body 50 may be injection molded using TPE elastomers or liquid rubber injected or casted using silicones. The hardness of the pliable material that forms adapter cap 30A, or the adapter cap material hardness, is sufficient to provide a cushioning surface, e.g., adapter exterior wall 52, which prevents irritation of a patient's skin while the patient is carrying a drug transfer assembly 10. Furthermore, the adapter cap material hardness is less than the first connector material hardness of the material that forms first connector 14.

In one embodiment, the adapter cap material hardness of the material that forms adapter cap 30A may have a hardness value on the Shore Durometer scale in the type A range for rubbers and softer plastics. In one exemplary embodiment, adapter cap 30A has a hardness range between Shore A 5 and Shore A 50. In another exemplary embodiment, adapter cap 30A has a hardness range between Shore A 20 and Shore A 40.

In one embodiment, the first connector material hardness of the material that forms first connector 14 may have a hardness value on the Shore Durometer scale in the type D range for harder plastics. In one exemplary embodiment, first connector 14 has a hardness range between Shore D 40 and Shore D 100. In another exemplary embodiment, first connector 14 has a hardness range between Shore D 50 and Shore D 80.

In one embodiment, adapter cap 30A is compatible with a Becton Dickinson ("BD") PhaSeal™ System available from Becton, Dickinson and Company of Franklin Lakes, N.J., the assignee of the present invention. In other embodiments, adapter cap 30A is compatible with other closed system drug transfer devices.

Referring to FIGS. 2A and 2B, in an exemplary embodiment, adapter cap 30 and first connector 14 are secured together by an interference fit connection to provide a secure fit therebetween, such that adapter cap 30 protectively surrounds and shields the first connector 14 to prevent contact between first connector 14 and the skin of a patient and to prevent contamination of the first connector 14 of the drug transfer assembly 10. Although adapter cap 30 as illustrated in FIGS. 2A and 2B is similar to an adapter cap 30B, illustrated in FIGS. 7A-7E, adapter cap 30A may be secured to first connector 14 in a similar manner.

Referring to FIGS. 2A, 2B, 6A-6F, and 7A-7E, adapter body 50 of adapter cap 30A and an adapter body 70 of adapter cap 30B are each sized and shaped to substantially correspond to an exterior profile 15 of first connector 14. This interference fit between adapter cap 30A, 30B, and first connector 14 is achieved by sizing and shaping the two mating parts, i.e., the interior profile of adapter body 50 of adapter cap 30A (or the interior profile of adapter body 70 of adapter cap 30B) and the exterior profile 15 of first connector 14 so that the interior profile of adapter body 50 of adapter cap 30A only slightly deviates dimensionally from the exterior profile 15 of first connector 14. This ensures an interference fit that secures adapter body 50 of adapter cap 30A (or adapter body 70 of adapter cap 30B) and first connector 14 together by a friction force after insertion of first connector 14 into a selected adapter cap 30.

Figure 7A:
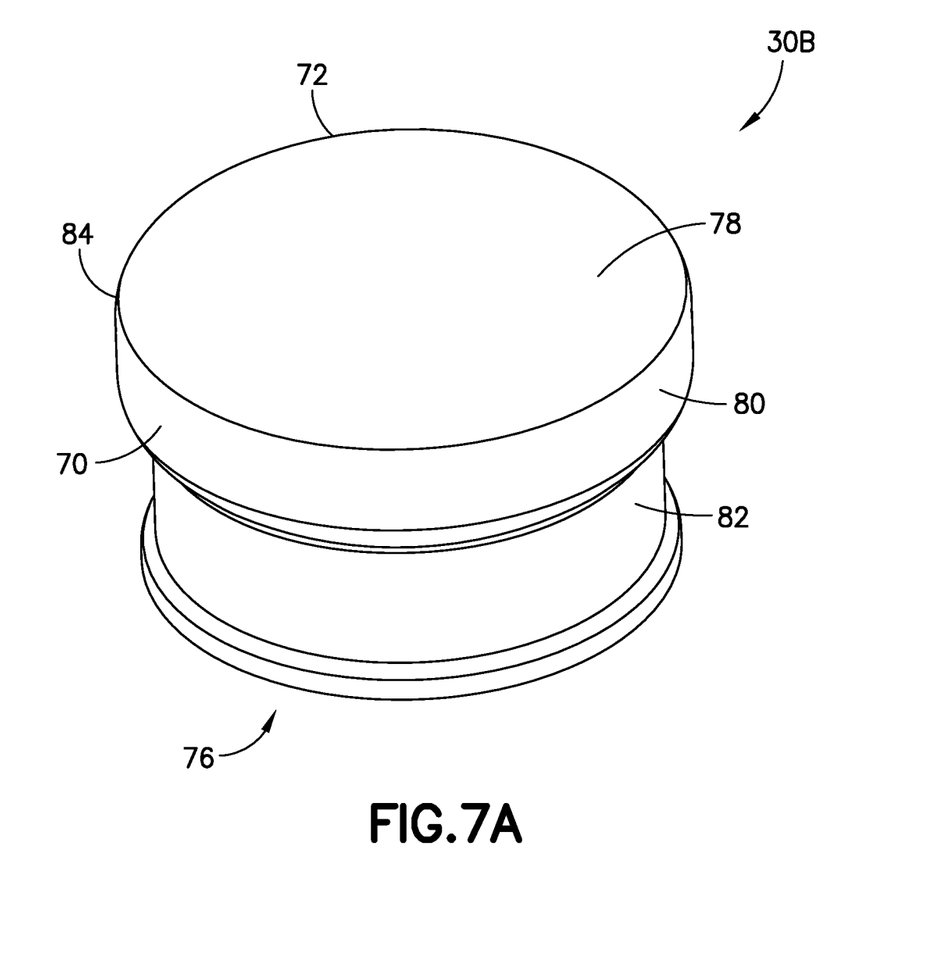
FIG. 7A is a perspective view of an adapter cap of a drug transfer assembly in accordance with an embodiment of the present invention.
Figure 7B:
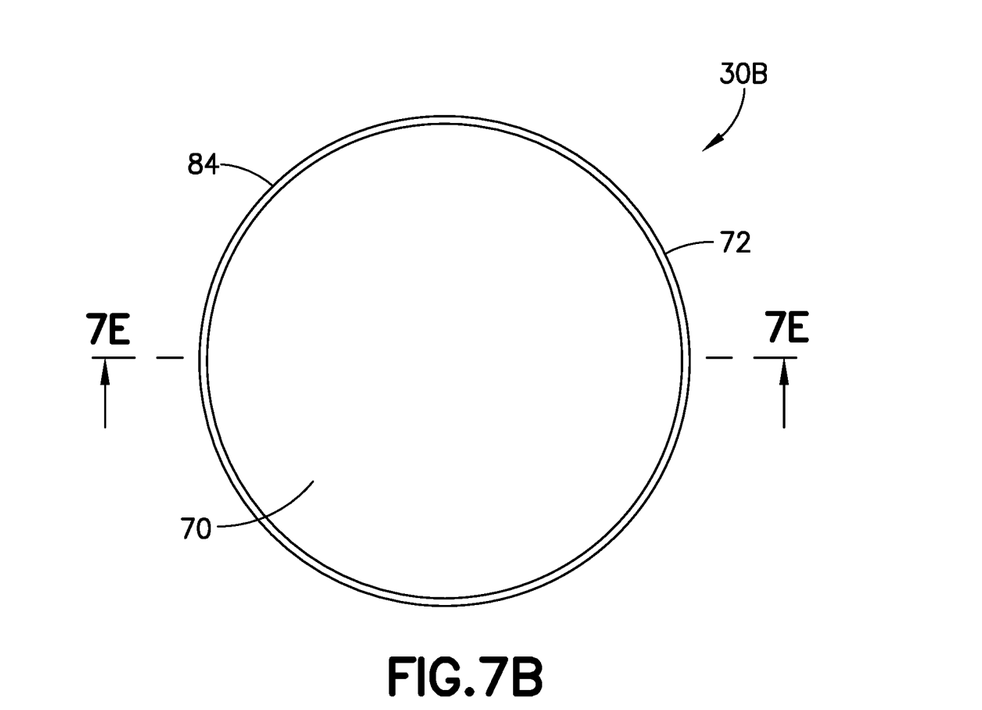
FIG. 7B is a bottom view of the adapter cap of FIG. 7A in accordance with an embodiment of the present invention.
Figure 7C:
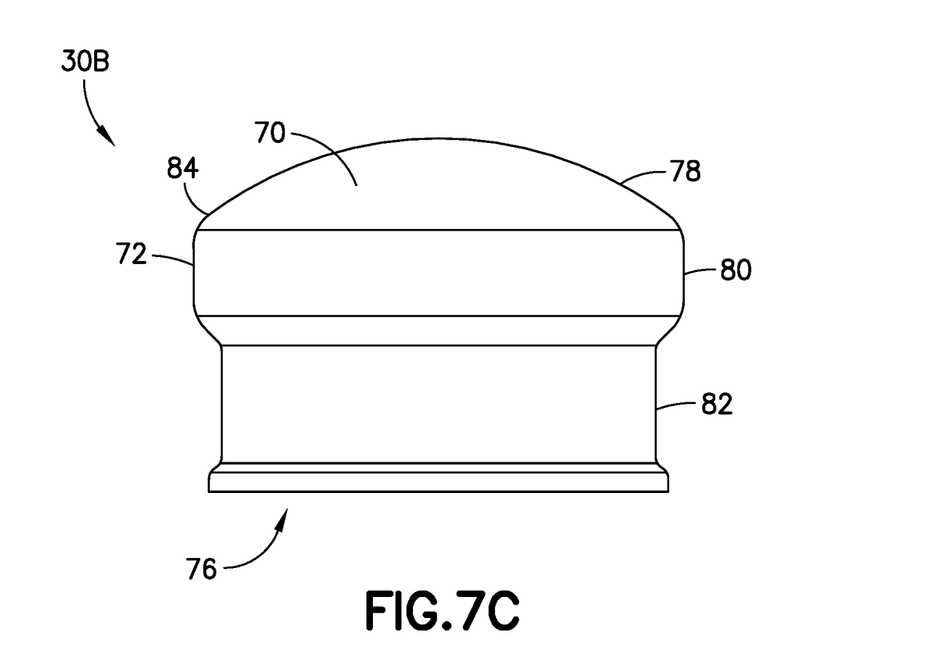
FIG. 7C is a side elevation view of the adapter cap of FIG. 7A in accordance with an embodiment of the present invention.
Figure 7D:
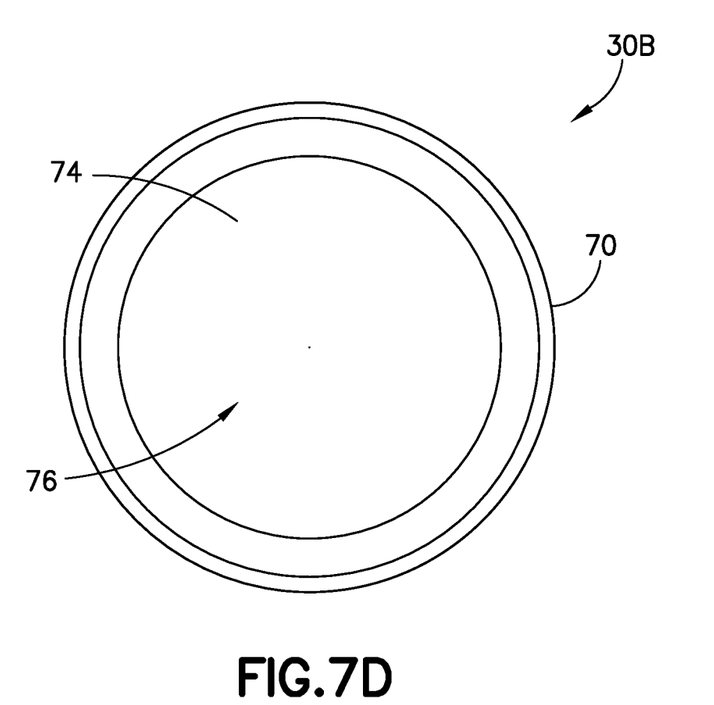
FIG. 7D is a plan view of the adapter cap of FIG. 7A in accordance with an embodiment of the present invention.
Figure 7E:
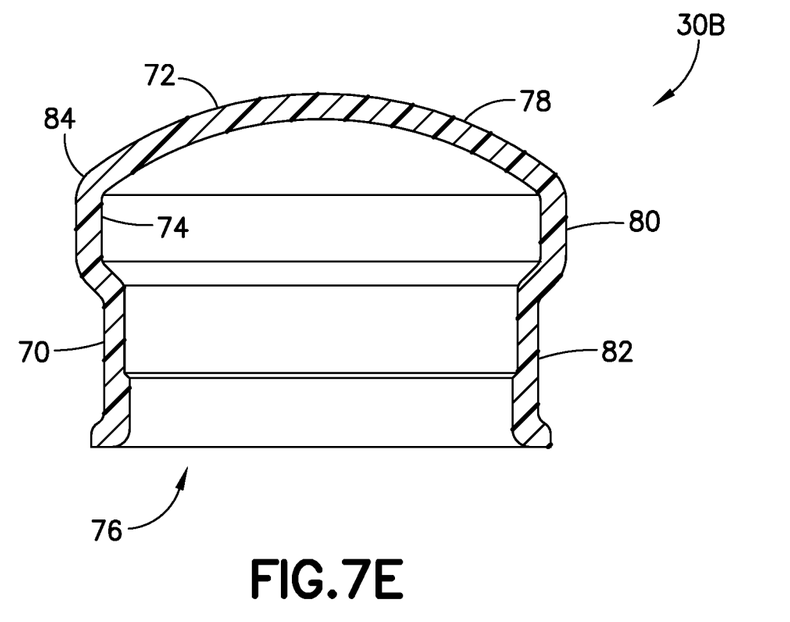
FIG. 7E is a cross-sectional view taken along line 7E-7E of the adapter cap of FIG. 7B in accordance with an embodiment of the present invention.

FIGS. 7A-7E illustrate adapter cap 30B according to another exemplary embodiment of the present disclosure. Adapter cap 30B generally includes adapter body 70 defining an adapter exterior wall 72 and an adapter interior wall 74, respectively corresponding to the exterior profile and the interior profile of adapter cap 30B. Referring to FIG. 7E, interior wall 74 defines a cavity 76 which is sized and shaped to receive first connector 14 via an interference fit connection as described above. Adapter body 70 generally includes an arcuate portion 78, a first cylindrical portion 80, a second cylindrical portion 82, and arcuate or curved edges 84. In this manner, adapter cap 30B does not have any sharp edges.

Adapter body 70 of an exemplary embodiment is preferably made of a pliable material, such as a soft rubber or pliable plastic, for example. In one exemplary embodiment, adapter body 70 is made from thermoplastic elastomers such as styrenic block copolymers, polyolefin blends & alloys, thermoplastic polyurethanes, thermoplastic copolyesters, thermoplastic polyamides, or similar materials. In other embodiments, adapter body 70 is made from thermosetting elastomers (rubbers) such as silicone, polyisoprene, neoprene, or similar materials. Adapter body 70 may be injection molded using TPE elastomers or liquid rubber injected or casted using silicones. The hardness of the pliable material that forms adapter cap 30B, or the adapter cap material hardness, is sufficient to provide a cushioning surface, e.g., adapter exterior wall 72, which prevents irritation of a patient's skin while the patient is carrying a drug transfer assembly 10. Furthermore, the adapter cap material hardness is less than the first connector material hardness of the material that forms first connector 14.

In one embodiment, the adapter cap material hardness of the material that forms adapter cap 30B may have a hardness value on the Shore Durometer scale in the type A range for rubbers and softer plastics. In one exemplary embodiment, adapter cap 30B has a hardness range between Shore A 5 and Shore A 50. In another exemplary embodiment, adapter cap 30B has a hardness range between Shore A 20 and Shore A 40.

In one embodiment, the first connector material hardness of the material that forms first connector 14 may have a hardness value on the Shore Durometer scale in the type D range for harder plastics. In one exemplary embodiment, first connector 14 has a hardness range between Shore D 40 and Shore D 100. In another exemplary embodiment, first connector 14 has a hardness range between Shore D 50 and Shore D 80.

In one embodiment, adapter cap 30B is compatible with a Becton Dickinson ("BD") PhaSeal™ System available from Becton, Dickinson and Company of Franklin Lakes, N.J., the assignee of the present invention. In other embodiments, adapter cap 30B is compatible with other closed system drug transfer devices.

Adapter caps 30A, 30B could be packaged separately from the other components of a drug transfer assembly 10. In another embodiment, adapter caps 30A, 30B could be "pre-packaged" and come already attached to a first connector 14 of a drug transfer assembly 10.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. An adapter cap and connector for a drug transfer assembly including the connector having a connector material hardness, the adapter cap removably connectable with the connector, the adapter cap having an adapter cap material hardness, wherein the adapter cap material hardness is less than the connector material hardness, the adapter cap having an exterior wall defined by a closed end portion, a first cylindrical portion having a first diameter, a second cylindrical portion having a second diameter that is smaller than the first diameter with respect to a vertical axis extending through the adapter cap, a continuous opening extending from the closed end portion through the first cylindrical portion and extending through the second cylindrical portion, and arcuate or curved edges transitioning the closed end portion to the first cylindrical portion such that the exterior wall forms a smooth surface extending from the end portion to at least the first cylindrical portion such that the exterior wall of the adapter cap is free from any sharp edges, wherein the first cylindrical portion is located between the closed end portion and the second cylindrical portion, and wherein with the adapter cap connected to the connector, the exterior wall defined by the first cylindrical portion, the second cylindrical portion, and the arcuate or curved edges of the adapter cap cooperate together to protectively surround and shield an exterior profile of the connector to prevent contact between the connector and the skin of a patient and to protectively shield the connector from contamination.

2. The adapter cap and connector of claim 1, wherein the connector comprises a rigid material and the adapter cap comprises a pliable material.

3. The adapter cap and connector of claim 1, wherein the adapter cap has a hardness range between Shore A 5 and Shore A 50.

4. The adapter cap and connector of claim 1, wherein the adapter cap has a hardness range between Shore A 20 and Shore A 40.

5. The adapter cap and connector of claim 1, wherein the connector includes a first cylindrical portion having a first connector diameter and a second cylindrical portion having a second connector diameter, the second connector diameter being smaller than the first connector diameter, and wherein the adapter cap is sized and shaped to substantially correspond to and encompass the exterior profile of the connector.

6. The adapter cap and connector of claim 1, wherein the connector has a first end connectable to a portion of an intravenous line adapted for connection to a bloodstream of a patient and a second end removably connectable with an injector.

7. A drug transfer assembly comprising: an intravenous line adapted for connection to a bloodstream of a patient; a connector connectable to a portion of the intravenous line, the connector having a connector material hardness; and an adapter cap removably connectable with the connector, the adapter cap having an adapter cap material hardness, wherein the adapter cap material hardness is less than the connector material hardness, the adapter cap having an exterior wall defined by a closed end portion, a first cylindrical portion having a first diameter, a second cylindrical portion having a second diameter that is smaller than the first diameter with respect to a vertical axis extending through the adapter cap, a continuous opening extending from the closed end portion through the first cylindrical portion and extending through the second cylindrical portion, and arcuate or curved edges transitioning the closed end portion to the first cylindrical portion such that the exterior wall forms a smooth surface extending from the end portion to at least the first cylinder portion such that the exterior wall of the adapter cap is free from any sharp edges, wherein the first cylindrical portion is located between the closed end portion and the second cylindrical portion, wherein with the adapter cap connected to the connector, the first cylindrical portion, the second cylindrical portion, and the arcuate or curved edges of the adapter cap cooperate together to protectively surround and shield an exterior profile of the connector to prevent contact between the connector and the skin of a patient and to protectively shield the connector from contamination.

8. The drug transfer assembly of claim 7, wherein the adapter cap has a frustoconical tapered portion.

9. The drug transfer assembly of claim 7, wherein the adapter cap has an adapter body which is sized and shaped to substantially correspond to and encompass the exterior profile of the connector to form an interference fit between the adapter cap and the exterior profile of the connector.

10. The drug transfer assembly of claim 7, wherein the connector comprises a rigid material and the adapter cap comprises a pliable material.

11. The drug transfer assembly of claim 7, wherein the injector comprises a syringe assembly.

12. The drug transfer assembly of claim 7, further comprising a second connector connected to a second portion of the intravenous line, the second connector adapted to receive an intravenous bag containing a second medication.

13. The drug transfer assembly of claim 7, wherein the adapter cap comprises a thermoplastic elastomer.

14. The drug transfer assembly of claim 7, wherein the adapter cap comprises a thermosetting elastomer.

15. The drug transfer assembly of claim 7, wherein the adapter cap has a frustoconical tapered portion that protectively surrounds at least a portion of the connector.

16. The drug transfer assembly of claim 7, wherein the connector includes a first cylindrical portion having a first connector diameter and a second cylindrical portion having a second connector diameter, the second connector diameter being smaller than the first connector diameter, and wherein the adapter cap is sized and shaped to substantially correspond to and encompass the exterior profile of the connector.

17. The drug transfer assembly of claim 7, further comprising an injector removably connectable with the connector, the injector containing a medication.

18. The drug transfer assembly of claim 17, wherein, with the injector connected to the connector, the connector provides a closed connection to the injector and the intravenous line and the injector is in fluid communication with the intravenous line via the connector thereby allowing injection of the medication to the bloodstream of the patient.

* * * * *